United States Patent
Petrick et al.

(10) Patent No.: US 6,343,112 B1
(45) Date of Patent: Jan. 29, 2002

(54) METHOD AND APPARATUS FOR REDUCING PHOTOCONDUCTIVE EFFECTS IN DUAL ENERGY APPLICATIONS OF SOLID STATE DIGITAL X-RAY DETECTORS

(75) Inventors: Scott William Petrick, Sussex; Anupama Somayaji, Waukesha, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/736,726

(22) Filed: Dec. 14, 2000

(51) Int. Cl.[7] ................................................. H05G 1/64
(52) U.S. Cl. ........................ 378/98.9; 378/62; 378/207
(58) Field of Search ................................. 378/98.9, 207, 378/98.2, 98, 62, 98.8, 4, 901; 382/131

(56) References Cited

U.S. PATENT DOCUMENTS

| | | | | |
|---|---|---|---|---|
| 5,901,198 A | * | 5/1999 | Crawford et al. | ............. 378/57 |
| 5,949,842 A | * | 9/1999 | Schafer et al. | ................. 378/4 |
| 5,970,113 A | * | 10/1999 | Crawford et al. | ............. 378/19 |
| 6,018,565 A | * | 1/2000 | Ergun et al. | .................. 378/95 |
| 6,067,342 A | * | 5/2000 | Gordon | ........................ 378/19 |
| 6,256,404 B1 | * | 7/2001 | Gordon et al. | .............. 382/131 |

* cited by examiner

*Primary Examiner*—Robert H. Kim
*Assistant Examiner*—Drew A. Dunn
(74) *Attorney, Agent, or Firm*—McAndrews, Held & Malloy; Peter J. Vogel; Michael A. Dellapenna

(57) ABSTRACT

A preferred embodiment of the present invention provides a method and apparatus for reducing photoconductive effects in dual energy applications of solid state digital x-ray detectors. The method comprises exposing a detector to a first exposure from an energy source and obtaining a first image data set during a first read time from the first exposure following a first delay. The method further comprises exposing the detector to a second exposure from the energy source and obtaining a second image data set during a second read time from the second exposure following a second delay. The first delay is less than the second delay. The first read time is less than the second read time.

23 Claims, 3 Drawing Sheets

METHOD AND APPARATUS FOR REDUCING PHOTOCONDUCTIVE EFFECTS IN DUAL ENERGY APPLICATIONS OF SOLID STATE DIGITAL X-RAY DETECTORS

CROSS REFERENCE TO RELATED APPLICATIONS (if applicable)

Not applicable.

STATEMENT REGARDING FEDERALLY SPONSORED RESEARCH & DEVELOPMENT (if applicable)

Not Applicable.

BACKGROUND OF THE INVENTION

The preferred embodiments of the present invention generally relate to dual energy medical diagnostic imaging systems, and in particular relate to a method and apparatus for reducing photoconductive effects of solid state digital x-ray detectors in dual energy medical diagnostic imaging systems.

X-ray imaging has long been an accepted medical diagnostic tool. X-ray imaging systems are commonly used to capture images, such as thoracic, cervical, spinal, cranial, and abdominal images that often include information necessary for a doctor to make an accurate diagnosis. X-ray imaging systems typically include an x-ray source and an x-ray sensor. When having a thoracic x-ray image taken, for example, a patient stands with his or her chest against the x-ray sensor as an x-ray technologist positions the x-ray sensor and the x-ray source at an appropriate height. X-rays produced by the source travel through the patient's chest, and the x-ray sensor then detects the x-ray energy generated by the source and attenuated to various degrees by different parts of the body. An associated control system obtains the detected x-ray energy from the x-ray sensor and prepares a corresponding diagnostic image on a display.

The x-ray sensor may be a conventional screen/film configuration, in which the screen converts the x-rays to light that exposes the film. The x-ray sensor may also be a solid state digital image detector. Digital detectors afford a significantly greater dynamic range than conventional screen/film configurations.

X-ray systems may be dual energy x-ray systems. The concept of dual energy is to take two exposures, one low energy and one high energy, to separate a low energy absorber (soft tissue) from a high energy absorber (bone). The two exposures are taken in rapid succession. The two exposures may be combined on an image pixel by image pixel (picture element) basis. Comparison of the two exposures produces improved detail contrast in soft tissue or bone.

One embodiment of a solid state digital x-ray detector may be comprised of a panel of semiconductor FETs and photodiodes. The FETs and photodiodes in the panel are typically arranged in rows (scan lines) and columns (data lines). A FET controller controls the order in which the FETs are turned on and off. The FETs are typically turned on, activated, in rows. When the FETs are turned on, charge to establish the FET channel is drawn into the FET from both the source and the drain of the transistor. Due to the imperfect nature of the amorphous silicon FETs, the charge is retained temporarily when the FET is turned off and bleeds out, decaying, over time, which corrupts the desired signal in the form of an offset. The source of each FET is connected to a photodiode. The drain of each FET is connected to read-out electronics via data lines. Each photodiode integrates the light signal and discharges energy in proportion to the x-rays absorbed by the detector. The gates of the FETs are connected to the FET controller. The FET controller allows signals discharged from the panel of photodiodes to be read in an orderly fashion. The read-out electronics convert the signals discharged from photodiodes. The energy discharged by the photodiodes in the detector and converted by the read-out electronics is used by an acquisition system to activate pixels in the displayed digital diagnostic image. The panel of FETs and photodiodes is typically scanned by row. The corresponding pixels in the digital diagnostic image are typically activated in rows.

The FETs in the x-ray detector act as switches to control the charging and discharging of the photodiodes. When a FET is open, an associated photodiode is isolated from the read-out electronics and is discharged during an x-ray exposure. When the FET is closed, the photodiode is recharged to an initial charge by the read-out electronics. Light is emitted by a scintillator in response to x-rays absorbed from the source. The photodiodes sense the emitted light and are partially discharged. Thus, while the FETs are open, the photodiodes retain a charge representative of the is x-ray dose. When a FET is closed, a desired voltage across the photodiode is restored. The measured charge amount to re-establish the desired voltage becomes a measure of the x-ray dose integrated by the photodiode during the length of the x-ray exposure.

X-ray images may be used for many purposes. For instance, internal defects in a target object may be detected. Additionally, changes in internal structure or alignment may be determined. Furthermore, the image may show the presence or absence of object s in the target. The information gained from x-ray imaging has applications in many fields, including medicine and manufacturing.

In any imagine system, x-ray or otherwise, image quality is important. In this regard, x-ray imaging systems that use digital or solid state image detectors ("digital x-ray systems") face certain unique difficulties. Difficulties in a digital x-ray image could include image artifacts, "ghost images," or distortions in the digital x-ray image. One source of difficulty faced by digital x-ray systems is the photoconductive characteristics of semiconductor devices used in the digital x-ray systems.

Photoconductivity is an increase in electron conductivity of a material through optical (light) excitation of electrons in the material. Photoconductive characteristics are exhibited by the FETs used as switches in solid state x-ray detectors. Ideally, FET switches isolate the photodiode from the electronics which measure the charge restored to the photodiode. FETs exhibiting photoconductive characteristics do not completely isolate the photodiode from the system, when the FETs are open. Consequently, the FETs transfer excess charge to the read-out electronics. If the FETs transfer excess charge to the read-out electronics, the energy subsequently discharged from the photodiodes to activate the pixels in the digital image may be affected. The unintended charge leakage through the FETs may produce artifacts or may add a non-uniform offset value to each of the pixels in the digital x-ray image, thus producing a line artifact in the image.

FETs and other materials made of amorphous silicon also exhibit a characteristic referred to as charge retention. Charge retention is a structured phenomenon and may be controlled to a certain extent. Charge retention corresponds to the phenomenon whereby not all of the charge drawn into the FET to establish a conducting channel is forced out when the FET is turned off. The retained charge leaks out of the FET over time, even after the FET is turned off, and the leaked charge from the FET adds an offset to the signal read out of the photodiodes by the x-ray control system.

The FETs in the x-ray detector exhibit charge retention characteristics when voltage is applied to the gates of the FETs to read the rows of the x-ray detector. The detector rows are generally read in a predetermined manner, sequence, and time interval. The time interval may vary between read operations for complete frames of the x-ray image. When a FET is opened after the charge on an associated photodiode is read by a charge measurement unit, the FET retains a portion of the charge. Between read operations, the charge retained by the FETs leaks from the FETs to a charge measurement unit. The amount of charge that leaks from the FETs exponentially decays over time. The next read operation occurs before the entire retention charge leaks from the FETs. Consequently, the charge measurement unit measures during each read operation an amount of charge that is retained by the FETs during the read operation for the present scan line. The charge measurement unit also reads an amount of charge that was stored by FETs that were activated in scan lines preceding (in time) the current scan line in both the current (detector) read operation and the preceding (detector) read operation.

The charge leaking from the FETs when a new read operation is initiated is referred to as the initial charge retention. The initial charge retention stored on multiple FETs, such as the FETs of a single data line, combines to form a charge retention offset for that column. The charge retention offset varies based on the rate at which rows of the x-ray detector panel are read. As the interval increases between read operations, the charge decay increases. As the panel rows are read, the charge retention offset builds to a steady state value. The steady state value for the charge retention rate represents the point at which the panel rows are read at a rate equaling the exponential decay rate of the charge on the FETs.

If the time between frames for both the offset and x-ray image are consistent, the effect of charge retention may be eliminated from the final image. In the normal process of reading a detector, the effect of retained charge may be minimized by simply subtracting the results of a "dark" scan from the results of an "exposed" scan. A "dark" scan is a reading done without x-ray. A "dark" scan simply activates the FETs on the x-ray detector panel. Thus, a "dark" scan may determine the charge retention characteristics exhibited by the FETs activated to read the x-ray detector. By subtracting the "dark" scan from the actual "exposed" scan of a desired object, the charge retention effects may be eliminated.

During an x-ray exposure, a similar phenomenon occurs whereby charge is generated in the FET as a result of the FET photoconductive characteristics. When the FETs are turned off at the end of the exposure, the additional charge also leaks out and adds to the read signal in a manner analogous to charge retention. However, the additional charge cannot be removed because the additional charge, resulting from the FET photoconductive characteristics, relates to the x-rays bombarding the x-ray detector. Thus, the additional charge resulting from the FET photoconductive characteristics is not predictable, nor is it reproducible in a "dark" image where no x-rays are transmitted. The number of FETs that photoconduct and the amount of charge conducted by the FETs are dependent upon the amount of x-ray exposure and the object imaged, as well as upon the individual properties of each FET. Since a solid state x-ray detector is structured along rows (scan lines) and columns (data lines), the excess charge in the FETs may result in structured image artifacts or offsets which cannot be corrected by contrasting the "exposed" image with a "dark" image.

Photoconductivity is not as structured as charge retention. First, when a FET in the x-ray detector is turned on to be read, the FET is always turned on with the same voltage. With the photoconductive effect, the "amount" that the FET is turned on is determined by the intensity of the light reaching a given FET. The light reaching the FETs may vary among a wide range of intensities for all of the FETs on the x-ray detector. Second, regardless of how strongly each FET is affected by photoconductivity (due to the light intensity at each FET), all of the FETs will be affected simultaneously. Charge retention induced by a read operation only stimulates a given FET or FETs in any given column at a time. Therefore, photoconductivity is much more unpredictable and is uncorrectable by a simple image subtraction method.

In a dual energy medical diagnostic imaging system, patient motion between the two exposures is a concern in the comparison of the two exposure images. The effects of patient motion may be reduced by reducing the time between exposures. The time between exposures is determined by the time to read out the detector. One solution to dealing with the photoconductive effect described above has been to delay reading the detector after the end of the exposure in order to allow the photoconductive effect to decay. However, the delay in reading the detector is at odds with reducing the time between exposures for dual energy imaging.

Thus, a need exists for a method and apparatus for reducing photoconductive effects of solid state digital x-ray detectors in dual energy medical diagnostic imaging systems.

BRIEF SUMMARY OF THE INVENTION

A preferred embodiment of the present invention provides a method and apparatus for reducing photoconductive effects in dual energy applications of solid state digital x-ray detectors. The method comprises exposing a detector to a first exposure from an energy source. The method further comprises obtaining a first image data set from the first exposure following a first delay. In a preferred embodiment, the first image data set is obtained during a first read time. The method further comprises exposing the detector to a second exposure from the energy source. The method further comprises obtaining a second image data set from the second exposure following a second delay. In a preferred embodiment, the second image data set is obtained during a second read time. Preferably, the first delay is less than the second delay, the first read time is less than the second read time, and the secondexposure is a brighter exposure than the first exposure. Preferably, the first image data set represents a darker image than the second image data set.

DETAILED DESCRIPTION OF THE INVENTION

Figure 1:
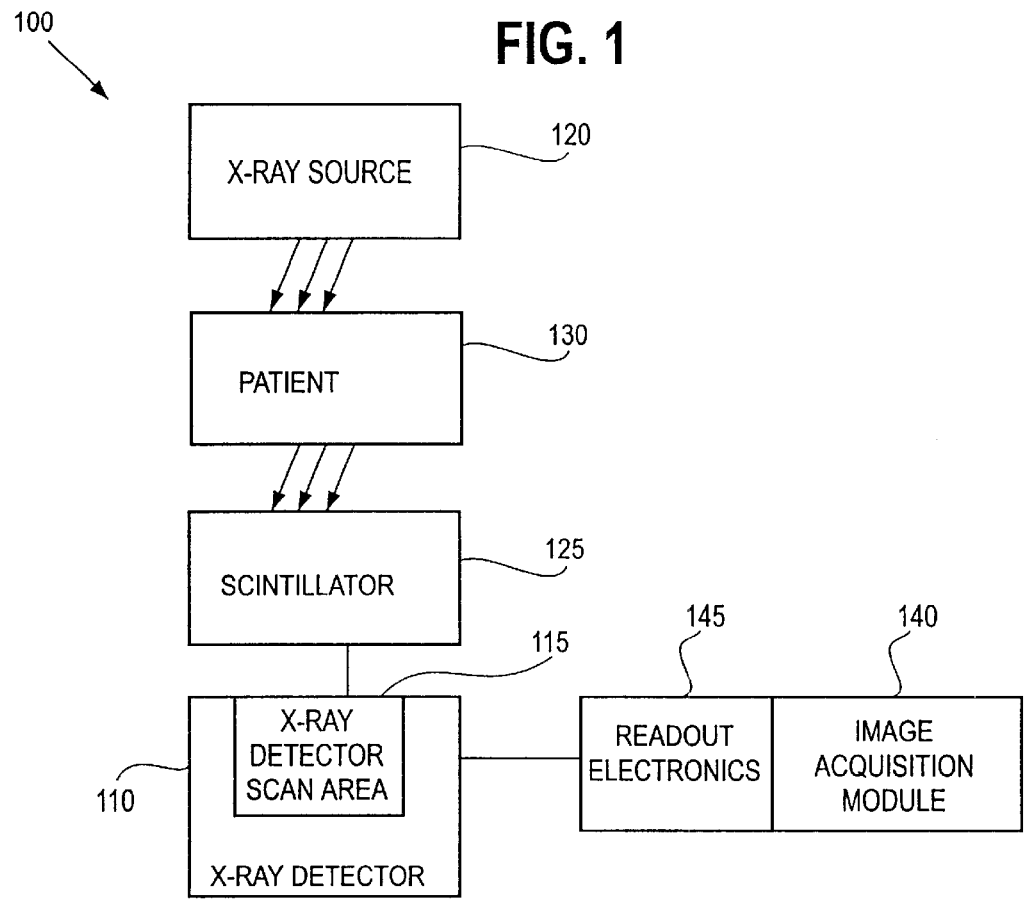
FIG. 1 illustrates a general medical diagnostic imaging system used in connection with a preferred embodiment of the present invention.

FIG. 1 illustrates a medical diagnostic imaging system 100 used in accordance with a preferred embodiment of the present invention. The medical diagnostic imaging system 100 includes a plurality of subsystems. For the purposes of illustration only, the medical diagnostic imaging system 100 is described as an x-ray system. The medical diagnostic imaging system 100 includes subsystems, such as an x-ray detector 110, an x-ray detector scan area 115, an x-ray source 120, a scintillator 125, and a patient 130. The medical diagnostic imaging system 100 also includes an image acquisition unit 140 with read-out electronics 145.

The patient 130 is positioned in the medical diagnostic imaging system 100. In one exemplary system, an x-ray source 120 is positioned above the patient 130. The x-ray detector 110 is positioned below the patient 130. The scintillator 125 is positioned between the patient 130 and the x-ray detector 110. X-rays are transmitted from the x-ray source 120 through the patient 130 to the scintillator 125. The scintillator 125 emits light in response to the x-rays transmitted from the x-ray source 120 through the patient 130. The emitted light is transmitted to the x-ray detector 110 and the x-ray detector scan area 115.

Figure 2:
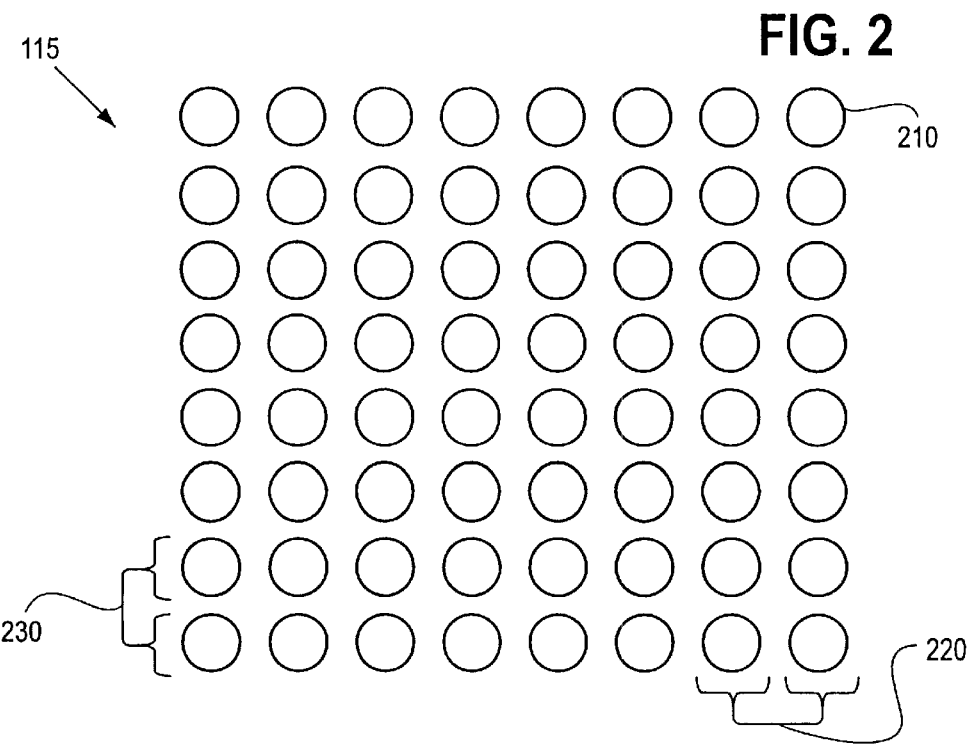
FIG. 2 illustrates a plan view of a solid state x-ray detector.

FIG. 2 illustrates a preferred embodiment of a solid state x-ray detector scan area 115 within an x-ray detector 110. The x-ray detector scan area 115 is comprised of cells 210 corresponding to pixels in an x-ray image. The cells 210 may be arranged in columns 220 and rows 230. The cells 210 are controlled by scan lines along row 230 and read out by data lines along column 220. One or more cells 210 are uniquely mapped to one or more pixels in an x-ray image. The pixels are activated to produce the desired digital x-ray image of the patient 130.

Figure 3:
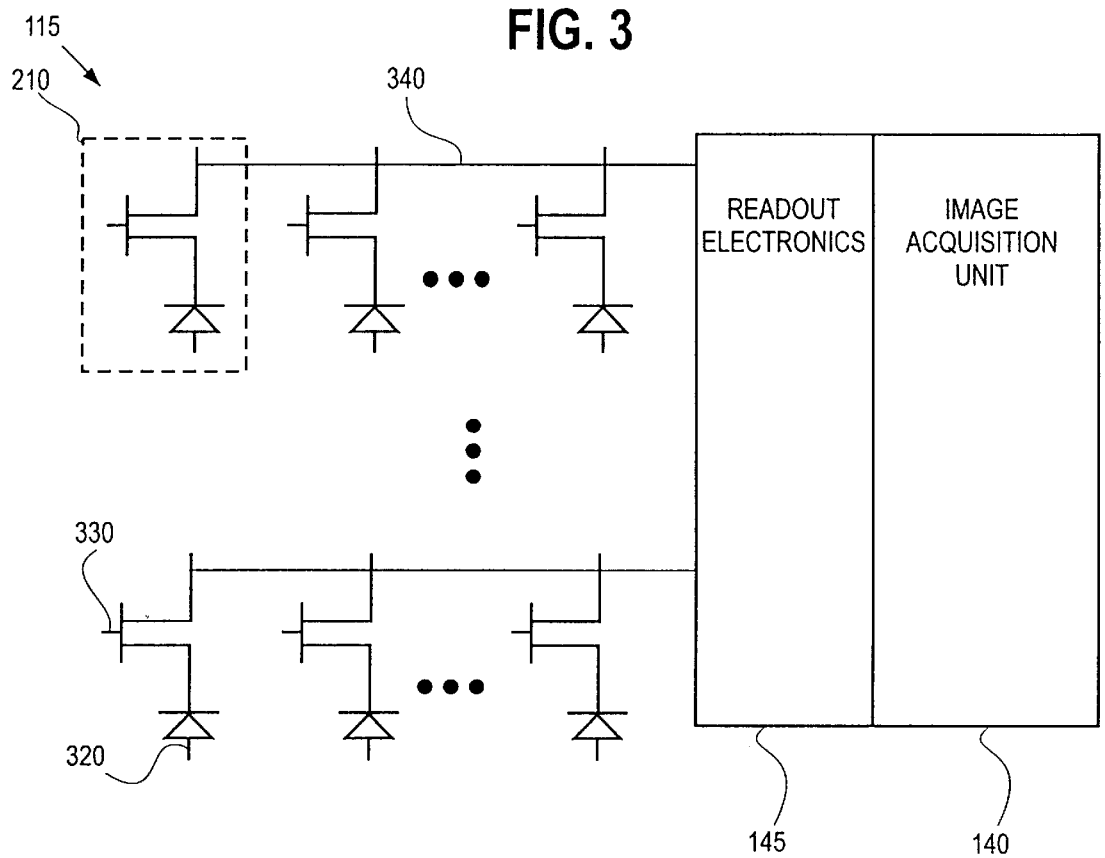
FIG. 3 illustrates a preferred embodiment of a solid state x-ray detector.

FIG. 3 illustrates a lower-level view of a preferred embodiment of a solid state x-ray detector scan area 115 within an x-ray detector 110. Each cell 210 comprises a photodiode 320 and a Field Effect Transistor (FET) 330. Data lines 340 connect the cells 210 to the read-out electronics 145 of the image acquisition module 140. Through the read-out electronics 145, the image acquisition unit 140 acquires an x-ray image from the x-ray detector scan area 115.

The image acquisition module 140 may acquire an x-ray image from the x-ray detector scan area 115 by receiving a signal from the data lines 340 from the cells 210 in the x-ray detector scan area 115. The signal from the data lines 340 may be generated by charge stored in the photodiodes 320. The charge stored in the photodiodes 320 may result from absorption of light by the photodiodes 320. The light is emitted by the scintillator 125 directly above the photodiodes 320 in response to absorption of x-ray energy by the scintillator 125. The FETs 330 allow the charge stored in the photodiodes 320 to travel as a signal through the data lines 340. The FETs 330 may be actuated by the FET controller (not shown) in the image acquisition module 140. The signal received by the image acquisition module 140 may include an offset produced by the charge retention characteristics and photoconductive effects of the FETs 330.

In order to reduce the photoconductive effect, a dark exposure may be first obtained. The photoconductive effect for the image resulting from the dark exposure is less than the photoconductive effect for a brighter image, which is the result of a brighter second exposure. By taking a "darker" exposure first, the photoconductive effect is reduced for the first image, and thus the delay time between exposures can be reduced. Also, the delay between the end of the second exposure and the beginning of the second detector read-out operation may be increased to reduce the photoconductive effect on the second image without any contribution to patient motion artifacts. Patient motion artifacts are reduced since the exposure-to-exposure delay time between two exposures is reduced.

In general, a dark image may be obtained first by lowering the exposure energy. However, the image produced by the exposure may be affected by factors such as the particular imaging technique, patient thickness, etc. Absorption characteristics of the detector 110 as a function of energy may also affect the image. Not all detectors 110 may be designed with the same parameters (CsI thickness, for example). Thus, one set of techniques may not produce exactly the same brightness across all detectors 110 with the same patient 130.

In a preferred embodiment, a timing mode, reducing the number of conversion levels for the darker image, can be defined to reduce the time to read the detector 110 between the two exposures. Since the image will be darker (by the design of the application), not as much dynamic range may be used to convert the signal from each pixel, and the number of conversion levels can be reduced. In a preferred embodiment, each additional conversion level costs one additional conversion clock time. A timing mode providing more conversion levels, and therefore more dynamic range at the expense of longer time to read the detector 110, can be defined for a second, brighter image, resulting from the second exposure.

Figure 4:
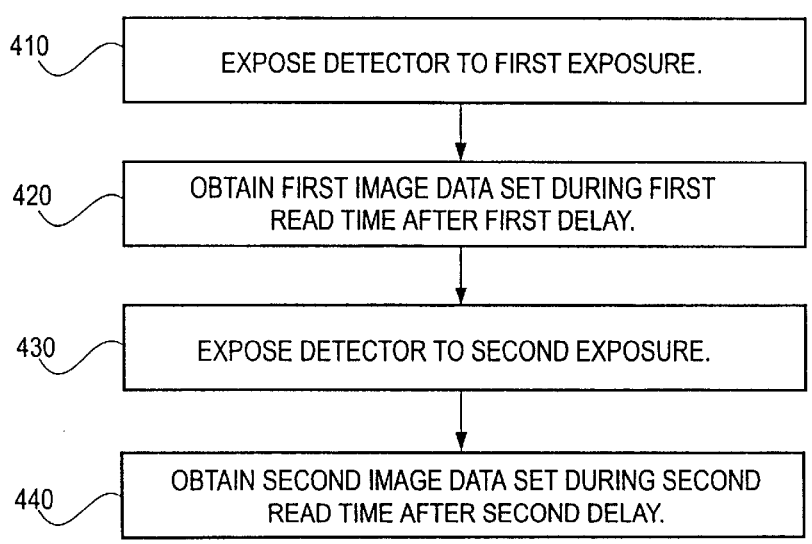
FIG. 4 illustrates a method for reducing offset effects in dual energy imaging.

FIG. 4 illustrates a method for reducing offset effects in dual energy imaging. In step 410, the detector 110 is exposed to a first exposure from an energy source 120. In a preferred embodiment, the first exposure is a lower dose exposure. Typically, a lower dose exposure will produce a darker image. A darker image may have less photoconductive effect than a brighter image. In step 420, a first set of image data is obtained from the first exposure. The first set of image data is obtained following a first delay. In a preferred embodiment, the first delay is the minimum delay to reduce the photoconductive effects of the darker image. Typically, photoconductive effects are less in a darker image than a brighter image. Thus, the delay time for a darker image is less than the delay time for a brighter image. In a preferred embodiment, the first delay is less than the "normal" delay time for a dual energy image acquisition system. In a preferred embodiment, the first set of image data is obtained from the detector 110 during a first read time. In a preferred embodiment, the first read time is less than the "normal" read time because the first image data set comprises a darker image data set with a smaller dynamic range than a normal image. The darker image with a smaller dynamic range may use fewer conversion levels to convert the data for each line 340 of the detector 110.

In step 430, the detector 110 is exposed to a second exposure from the energy source 120. In a preferred embodiment, the second exposure is a higher dose exposure.

Typically, a higher dose exposure will produce a brighter image. In step 440, a second set of image data is obtained from the second exposure. The second set of image data is obtained following a second delay. In a preferred embodiment, the second delay is typically longer than the first delay. The second set of image data is obtained from the detector 110 during a second read time. The second read time is longer than the first read time. The brighter image has a larger dynamic range than the darker image. The larger dynamic range may use more conversion levels than the darker image.

Figure 5:
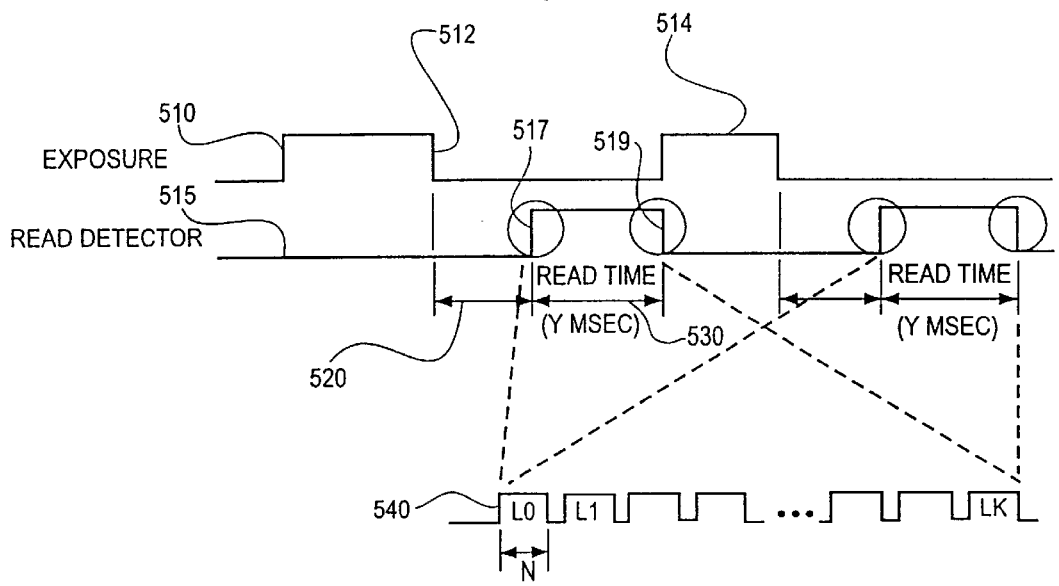
FIG. 5 illustrates a first exemplary dual energy image acquisition sequence for a detector that exhibits photoconductive charge retention.

FIG. 5 illustrates a first exemplary dual energy image acquisition sequence for a detector 110 that exhibits photoconductive charge retention. Line 510 denotes the exposure control signal that controls exposure sequence and timing wherein the x-ray source is turned on when exposure signal 510 is high and off when the signal 510 is low. Line 515 denotes an acquisition control signal that controls the sequence and timing with which data is read from the detector. The acquisition control signal 515 remains off (low) until a read initiate time 517. The acquisition control signal 515 changes state (from off to on) at read initiate time 517 to cause the detector to begin reading data from the cells of the detector line by line. The rows of the detector are sequentially read-out until read end time 519. The interval between read initial and end times 517 and 519 represent the read time. The acquisition sequence uses uniform delays 520 from the end 512 of the exposure 510 to the read initiate time 517 to allow the photoconductive charge retention to decay (T milliseconds) to a predetermined desired level. The acquisition sequence shown in FIG. 5 uses a uniform number of conversion levels 540 (N) during each and every detector 110 read operation for each scan line for each of the two exposures 510 and 514. Using the same number of conversion levels 540 (N) during each and every read operation results in a read time 530 of Y milliseconds after every exposure pulse 510 and 514.

Figure 6:
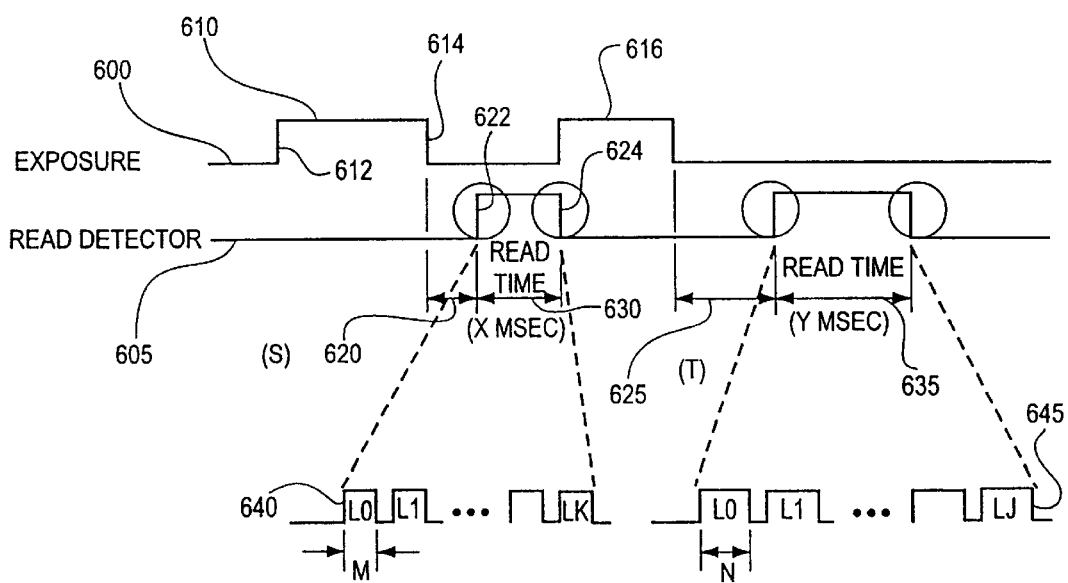
FIG. 6 illustrates a second exemplary dual energy image acquisition sequence for a detector that exhibits photoconductive charge retention.

FIG. 6 illustrates a preferred embodiment for a dual energy image acquisition sequence for a detector 110 that exhibits photoconductive charge retention. Line 600 denotes an exposure control signal that turns the x-ray source on when high and off when low. Line 605 denotes an acquisition control line that causes a read-out operation of the detector 110 to occur line by line during the conversion pulses 640. The exposure pulse 610 begins at time 612 and ends at time 614. A delay 620 follows the exposure end time 614 before the read initiate time 622 starting a read interval 630. The read interval 630 continues until read stop time 624. A second exposure pulse 616 begins at the read stop time 624.

During the first read interval 630, a first series of energy conversion pulses LO to LK 640 are produced. Each conversion pulse 640 in the first series has a predetermined length representing a given number of conversion levels (M). A second read interval 635 includes a second series of energy conversion pulses/level LO to LK 645, where K represents the number of scan lines, or the number of times M (or N) conversion levels are repeated. Each conversion pulse 645 in the second series has a predetermined length representing a number of conversion levels (N). The length of the conversion pulses 640 may be shorter than the length of the conversion pulses 645. Varying the length of conversion pulses 640 and 645 causes the first and second read intervals 630 and 635 to be different in length. For instance the first read interval 630 may be shorter than the second read interval 635.

In the embodiment of FIG. 6, delays 620 and 625 represent exposure to acquisition delays following first and second exposure pulses 610 and 616, respectively. The first delay 620 is shorter than the second delay 625. The length f the exposure pulses 610 and 616 may vary as will the intensity of the exposure, and thus, the length of the first and second delays 620 and 625 may be varied by associated amounts, respectively. The acquisition sequence may be implemented when the exposure 610 yielding the darker image is made first. The darker image exposure 610 may have less photoconductive charge retention than the brighter image from the second exposure 616. Since the darker image exposure 610 may have less photoconductive charge retention than the brighter image exposure 616, the first exposure-to-acquisition delay 620 added to allow for decay of photoconductive charge retention may be reduced (to S, where S<T).

Since the first image will be darker, shorter conversion pulses 640 may be used (K conversion pulses 640 of M length, where M<N). Since shorter conversion pulses 640 may be used, a shorter time may be used to convert the data for each line 340. Since a shorter time may used to covert the data for each line, the time 630 to read the detector 110 may be shorter (X milliseconds, where X<Y). The time between exposures, useful in limiting the effects of patient 130 motion, may be reduced from T+Y milliseconds to S+X milliseconds. If the detector 110 does not suffer from photoconductive charge retention, delay 620 from the end of the exposure 610 to the beginning of the detector read may be reduced (perhaps to 0). The number of conversion pulses 640 and, thus, the time 630 to read the detector 110 may be reduced from Y to X milliseconds. For the second, brighter image, the delay 625 may be increased to account for increased photoconductive charge retention. The brighter image may require longer conversion pulses 645 (K conversion levels 645 of N length). The time 635 to read the detector 110 for the brighter image may be lengthened.

Thus, the preferred embodiments provide a simple solution to what has become a serious degradation issue for solid state x-ray detectors. The method and apparatus of the preferred embodiments for reducing photoconductive effects in dual energy applications of solid state digital x-ray detectors may improve the design of new medical diagnostic imaging systems and may preserve existing medical diagnostic imaging systems through photoconductive offset reduction while minimizing the effects of patient motion.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for reducing offset effects in dual energy imaging, said method comprising:

exposing a detector to a first exposure from an energy source during a first exposure interval;

after said first exposure interval, waiting a first delay time before obtaining a first image data set from said first exposure during a first acquisition interval;

after said first acquisition interval, exposing said detector to a second exposure from said energy source during a second exposure interval; and after said second exposure interval, waiting a second delay time before obtaining a second image data set from said second exposure during a second acquisition interval, wherein said first and second delay times are not equal in length.

2. The method of claim 1, wherein said energy source comprises an x-ray energy source.

3. The method of claim 1, wherein said detector comprises a solid state digital x-ray detector.

4. The method of claim 1, wherein said first exposing step comprises using a lower energy exposure than said second exposing step.

5. The method of claim 1, wherein said first exposing step comprises using a lower energy exposure.

6. The method of claim 1, wherein said second exposing step comprises using a higher energy exposure.

7. The method of claim 1, wherein said first delay time is less than said second delay.

8. The method of claim 1, wherein said first delay time comprises a reduced delay.

9. The method of claim 1, wherein said first obtaining step includes obtaining a darker image data set than said second obtaining step.

10. The method of claim 1, wherein said second obtaining step includes obtaining a bright image data set.

11. The method of claim 1, further comprising:

obtaining said first image data set during a first read time; and obtaining said second image data set during a second read time.

12. The method of claim 11, wherein said first read time is less than said second read time.

13. The method of claim 11, wherein said first read time comprises a reduced read time.

14. A method for reducing offset effects in dual energy imaging, said method comprising:

exposing a detector to at first exposure from an energy source;

obtaining a first image data set from said first exposure following a first delay;

exposing said detector to at second exposure from said energy source, said second exposure being, greater than said first exposure; and obtaining a second image data set from said second exposure following a second delay, said second delay differing from said first delay.

15. The method of claim 14, wherein said energy source comprises an x-ray energy source.

16. The method of claim 14, wherein said detector comprises a solid state x-ray digital detector.

17. The method of claim 14, wherein said first image data set comprises a darker image data set.

18. The method of claim 14, wherein said second obtaining step obtains a brighter image data set.

19. A method for reducing offset effects in dual energy imaging, said method comprising:

exposing, a detector to a first exposure from an energy source;

obtaining a first imagine data set from said first exposure during a first read time;

exposing said detector to a second exposure from said energy source, said second exposure being greater than said first exposure; and obtaining a second image data set from said second exposure during a second read time, said second read time differing from said first read time.

20. The method of claim 19, wherein said energy source comprises an x-ray energy source.

21. The method of claim 19, wherein said detector comprises a solid state x-ray digital detector.

22. The method of claim 19, wherein said first image obtaining step obtains a dark image data set.

23. The method of claim 19, wherein said second obtaining step obtains a bright image data set.

* * * * *